United States Patent
Yong et al.

(10) Patent No.: US 8,498,697 B2
(45) Date of Patent: Jul. 30, 2013

(54) CLASSIFICATION OF SOMATOSENSORY EVOKED POTENTIAL WAVEFORMS

(75) Inventors: Hu Yong, Hong Kong (HK); Luk Keith D. K., Pokfulam (HK)

(73) Assignee: The University of Hong Kong, Hong Kong (HK)

( * ) Notice: Subject to any disclaimer, the term of this patent is extended or adjusted under 35 U.S.C. 154(b) by 309 days.

(21) Appl. No.: 12/916,472

(22) Filed: Oct. 29, 2010

(65) Prior Publication Data

US 2011/0105939 A1 May 5, 2011

Related U.S. Application Data

(60) Provisional application No. 61/256,795, filed on Oct. 30, 2009.

(51) Int. Cl.
*A61B 5/04* (2006.01)

(52) U.S. Cl.
USPC .......................................................... 600/544

(58) Field of Classification Search
USPC ................................................. 600/544, 545
See application file for complete search history.

(56) References Cited

U.S. PATENT DOCUMENTS

| | | | | |
|---|---|---|---|---|
| 4,279,258 A | * | 7/1981 | John ............................... | 600/544 |
| 4,603,703 A | * | 8/1986 | McGill et al. ................... | 600/544 |
| 4,705,049 A | * | 11/1987 | John ............................... | 600/544 |
| 4,913,160 A | | 4/1990 | Erwin | |
| 5,846,208 A | * | 12/1998 | Pichlmayr et al. ............ | 600/544 |
| 2006/0241562 A1 | * | 10/2006 | John et al. ....................... | 604/503 |
| 2008/0243022 A1 | * | 10/2008 | Donnett et al. ................ | 600/544 |
| 2008/0269835 A1 | * | 10/2008 | Carlson et al. .................. | 607/45 |
| 2009/0264786 A1 | * | 10/2009 | Jacquin ........................... | 600/544 |

FOREIGN PATENT DOCUMENTS

WO WO/2006/013585 2/2006

OTHER PUBLICATIONS

Automatic Artifact Rejection during Intraoperative Recording of Somatosensory Evoked Potentials (Simard JM, Friedman WA), Neurosurg. vol. 61, Sep. 1984 pp. 609-611.
Intraoperative Neurological Monitoring (From the IEEE Engineering in Medicine and Biology Magazine), IEEE Engineering in Medicine and Biology Magazine. Jul./Aug. 2006. pp. 39-45.
Magnetoencephalographic artifact identification and automatic removal based on independent component analysis and categorization approaches, Journal of Neuroscience Methods. vol. 157, issue 2. Oct. 30, 2006. pp. 337-354.
Removal of ocular artifacts from electro-encephalogram by adaptive filtering, Medical and Biological Engineering and Computing, vol. 42 No. 3, May 2004. pp. 407-412.
Semi-Automatic Artifact Rejection Procedure based on Kurtosis, Renyi's Entropy and Independent Component Scalp Maps, (Antonino Greco, Nadia Mammone, Francesco Carlo Morabito, and Mario Versaci,) World Academy of Science, Engineering and Technology 7, 2005.
Clinical Evaluation of a Method for Automatic Detection and Removal of Artifacts in Auditory Evoked Potential Monitoring (Nicole A. M. de Beer, MSc, Maarten van de Vetde, MSc, and Pierre J. M. Cluitmans, PhD), Journal of Ctinical Monitoring vol. 11 No. 6,Nov. 1995: pp. 381-391.

(Continued)

*Primary Examiner* — Navin Natnithithadha
*Assistant Examiner* — Etsub Berhanu
(74) *Attorney, Agent, or Firm* — Berkeley Law & Technology Group, LLP

(57) ABSTRACT

Embodiments are disclosed relating to classification of somatosensory evoked potential waveforms.

27 Claims, 13 Drawing Sheets

OTHER PUBLICATIONS

Spinal Cord Monitoring During Surgery by Direct Recording of Somatosensory Evoked Potentials, J Nerosurg, vol. 60, Feb. 1984, pp. 440-443.

Permutation entropy of the electroencephalogram: a measure of anaesthetic drug effect, British Journal of Anesthesia, vol. 101 No. 6, Dec. 2008. pp. 810-821.

Automatic artifact rejection for EEG data using high-order statistics and independent component analysis, by Delorme A, Makeig S, Sejnowski TJ. Paper presented at: International workshop on ICA; San Diego, CA. 2001.

EEG Windowed Statistical wavelet Deviation for Estimation of Muscular Artifacts, by Vialatte F, Solé-Casals J, Cichocki A. Physiological Measurements 2008, 29(12):1435-1452.

Somatosensory Evoked Potentials, General Principles. By Alan D Legatt, MD, Ph., as retrieved from http://emedicine.medscape.com/article/1139906-print on Oct. 30, 2010. pp. 1-37.

Guideline 9D: Guidelines on short-latency somatosensory evoked potentials, Journal Clinical Neurophysiology. Apr. 2006;23(2): pp. 168-179.

Rating Form for Physical and Biological Constructs (Pathologies and Impairments) and their Implications for Diagnosis, Health, Function, and QOL,as retrieved from http://www.asia-spinalinjury.org/bulletinBoard/ASIA2007SEPStokicCurt.pdf, Sep. 2007, pp. 1-13.

Time-frequency component analysis of somatosensory evoked potentials in rats. By Zhi-Guo Zhang, Jun-Lin Yang, Shing-Chow Chan, Keith Dip-Kei Luk, and Yong Hu. BioMedical Engineering OnLine 2009, 8:4. pp. 1-10.

Multichannel PC Based Data Acquisition System for High-Resolution EEG, IEEE Transactions on Biomedical Engineering, vol. 42 Issue: 12, Dec. 1995.

Removal of power-line interference from the ECG: a review of the subtraction procedure. By Chavdar Levkov, Georgy Mihov, Ratcho Ivanov, Ivan Daskalov, Ivaylo Christov, and Ivan Dotsinsky. BioMedical Engineering OnLine 2005, 4:50. pp. 1-18.

Casual Filter Application in the Subtracting Method for Power-Line Interference Removing from ECG. Conference on Electronics, Sozopol, Bulgaria. Sep. 2008.

Noise Removal from Surface Respiratory EMG Signal. By Slim Yacoub, Kosai Raoof. International Journal of Computer, Information, and Systems Science, and Engineering 2:4. 2008. pp. 226-233.

Guidelines for Somatosensory Evoked Potentials, as retrieved from http://web.archive.org/web/20061028174002/http://www.aanem.org/documents/SEPGuidelines.pdf at Internet Archive dated Oct. 2006. pp. 1-24.

Eliminating cardiac contamination from myoelectric control signals developed by targeted muscle reinnervation. By Ping Zhou and Todd A Kuiken. Physiol. Meas. 27 (2006). pp. 1311-1327.

Processing EMG. By David Deleon. Retrieved from faculty.unlv.edu/jmercer/Seminar%20presentation/Processing.ppt Oct. 2010.

* cited by examiner

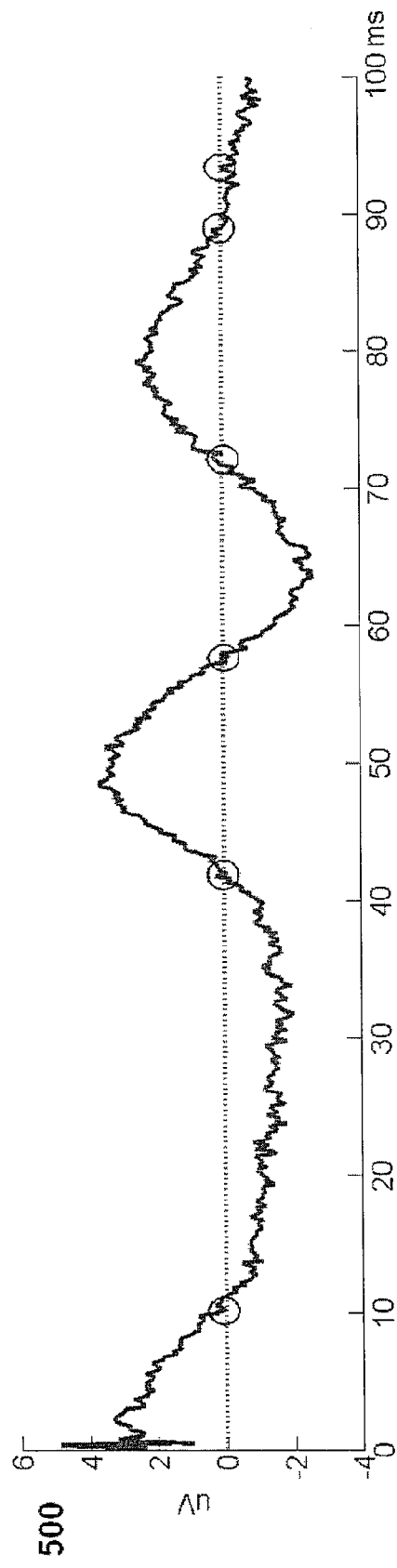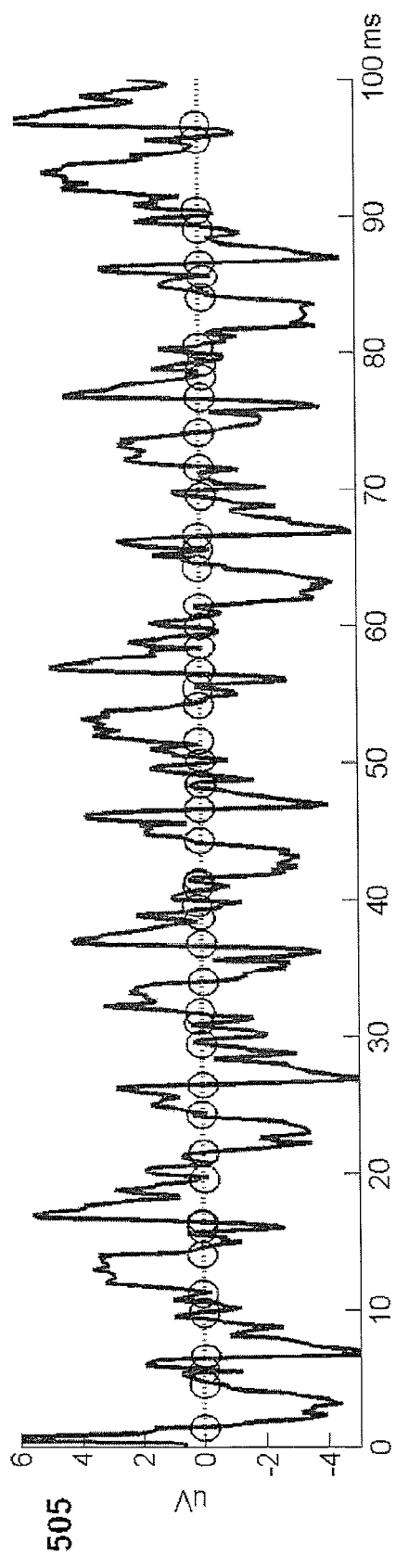

CLASSIFICATION OF SOMATOSENSORY EVOKED POTENTIAL WAVEFORMS

CROSS-REFERENCE TO RELATED APPLICATION

This application claims priority to provisional patent application Ser. No. 61/256,795, entitled "Classification of Sematosensory Evoked Potential Waveforms," filed on Oct. 30, 2009, and which is incorporated by reference herein in its entirety and which is assigned to the assignee of the currently claimed subject matter.

BACKGROUND

1. Field

The subject matter disclosed herein relates to classification of somatosensory evoked potential waveforms.

2. Information

Individuals who may have had injuries to their peripheral nerve, spinal cord, brain stem, or primary somatosensory cortex may be examined to detect severity of an injury or to monitor neural structures within their somatosensory pathways. One way of examining the integrity and functional status of the somatosensory nerve pathway is by monitoring evoked potentials. In this context, the term "evoked potentials" is intended to refer to electrical responses generated by an individual's nervous system in response to sensory stimuli. Somatosensory evoked potentials (SEPs) may comprise of a series of waves that may reflect sequential activation of neural structures along somatosensory pathways.

A dorsal column-lemniscal system may comprise an anatomical substrate of SEPs within a Central Nervous System. Intraoperative SEP monitoring in this context refers to techniques used for reducing risks of iatrogenic injury to a spinal cord during spinal surgery or neurosurgery, for example. SEP waveforms may be recorded and evaluated. However, SEP recordings may be accompanied by noise signals which may decrease quality of an SEP recording, making identification of one or more peak signal values of an SEP recording more challenging. Such noise signals, for example, may affect accuracy of latency/amplitude measurements or undermine methods of processing SEP recordings, for example. Such noise signals, also referred to in this context as artifacts, may comprise relative transient phenomena from physiologic or non-physiologic sources.

BRIEF DESCRIPTION OF DRAWINGS

Non-limiting and non-exhaustive aspects are described with reference to the following figures, wherein like reference numerals refer to like parts throughout the various figures unless otherwise specified.

FIGS. 5A and 5B show an example calculation of zero-crossing points in SEP recordings according to an implementation.

DETAILED DESCRIPTION

Figure 1A:
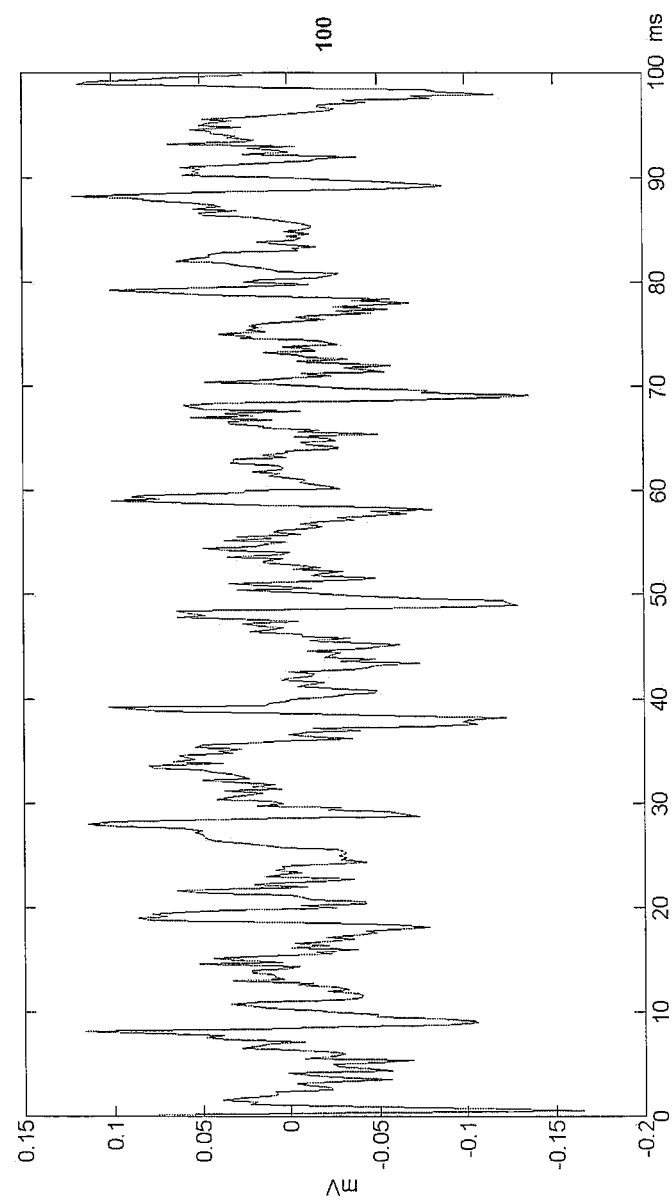
FIGS. 1A-C illustrate examples of noise signals extracted from SEP recordings.

Some portions of the detailed description are presented in terms of algorithms or symbolic representations of operations on binary digital signals stored within a memory of a specific apparatus or special purpose computing device or platform. In the context of this particular specification, the term specific apparatus or the like includes a general purpose computer or other computing device once it is programmed to perform particular functions pursuant to instructions from program software. Algorithmic descriptions or symbolic representations are examples of techniques used by those of ordinary skill in the signal processing or related arts to convey the substance of their work to others skilled in the art. An algorithm is here, and generally, considered to be a self-consistent sequence of operations or similar signal processing leading to a desired result. In this context, operations or processing involves physical manipulation of physical quantities. Typically, although not necessarily, such quantities may take the form of electrical or magnetic signals capable of being stored, transferred, combined, compared or otherwise manipulated.

It has proven convenient at times, principally for reasons of common usage, to refer to such signals as bits, data, values, elements, symbols, characters, terms, numbers, numerals or the like. It should be understood, however, that all of these or similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device. For example, a specific computing apparatus may comprise one or more processors programmed with instructions to perform one or more specific functions.

A method or system is provided for classifying somatosensory evoked potential (SEP) recordings of SEP waveforms. An "SEP waveform," as used herein, may refer to a series of electrical waves that may indicate sequential activation of neural structures along somatosensory pathways. Such somatosensory pathways may be located, for example, within a human spinal cord. Typically, an SEP recording may refer to one or more recorded signals comprising a combination of one or more SEP signal waveforms and one or more noise signal waveforms. Thus, for example, an SEP recording be stored in a digital format in a memory device, as an example. In at least some embodiments, as suggested previously, recordings may be created in an environment that may also result in one or more noise signal waveforms along with one or more SEP signal waveforms. As mentioned previously, an SEP recording may be obtained from an individual's somatosensory pathways.

In embodiments in accordance with claimed subject matter, as described in more detail below, SEP recordings may be classified based at least in part on certain characteristics. Without limitation, examples of such characteristics may include time-based (temporal) or frequency-based characteristics. Such characteristics, for example, may be employed to make determinations regarding SEP recordings of sufficient quality to be employed to evaluate an individual's somatosensory pathways, for example.

In some situations, an SEP recording may be sufficiently affected by ambient noise signals that it may be more effective to discard the particular recording. For example, in some embodiments, an SEP composite recording may be obtained by averaging or otherwise filtering or processing sufficiently suitable SEP recordings. However, an SEP recording sufficiently affected by noise to warrant discarding may degrade even an SEP composite recording, for example. Therefore, by omitting such SEP recordings for example, SEP composite recordings may be obtained by averaging a smaller number of suitable SEP recordings than if such SEP recordings were included, as an example.

An "artifact," as used herein, may refer to one or more noise signal waveforms which may affect an SEP recording. Artifacts may comprise transient phenomena from physiologic or non-physiologic sources, for example.

SEP recordings containing sufficient artifacts to impact evaluation of an individual's somatosensory pathways, for example, may be detected and potentially omitted, if desired. Having such a capability, for example, may permit SEP recordings to be taken over a period of time in which such SEP recordings are not overly influenced or affected by the presence of noise signals in the SEP recordings.

For example, an SEP recording in some circumstances may include a signal amplitude or enough artifacts at a level so that degradation of the SEP recording may be difficult to compensate or adjust through signal processing. Signal processing, typically in the form of signal averaging or signal filtering, for example, refers to techniques used to distinguish between an SEP signal waveform and a noise signal waveform. For example, noise signal waveforms may be produced at least in part by spurious or background electrical signals picked up by recording electrodes. If this happens, typically, such noise signals are combined with SEP signal waveforms as a part of the recording process that produces an SEP recording, for example. Artifact rejection in this context refers to detecting and omitting those SEP recordings with sufficient levels of noise signals that it would difficult to compensate or adjust through signal processing for degradation of an SEP composite recording if the SEP composite recording were to include those SEP recordings. Artifact detection and omission, therefore, may comprise an effective tool for selecting SEP recordings for a SEP composite recording.

An SEP recording may be affected by the presence of one or more noise signal waveforms. In one particular embodiment, an SEP composite recording may be generated by averaging several individual SEP recordings. In this context, however, the term averaging includes weighted averaging or other types of signal filtering approaches, such as, for example, high-pass filtering, law-pass filtering, FIR filtering or HR filtering, to provide only a few examples. By averaging several SEP recordings, influence by a particular noise signal waveform present may be reduced. An SEP composite recording, for example, that may be produced, may be evaluated to determine at least in part operability or health of neural structures along an individual's somatosensory pathways.

Figure 1B:
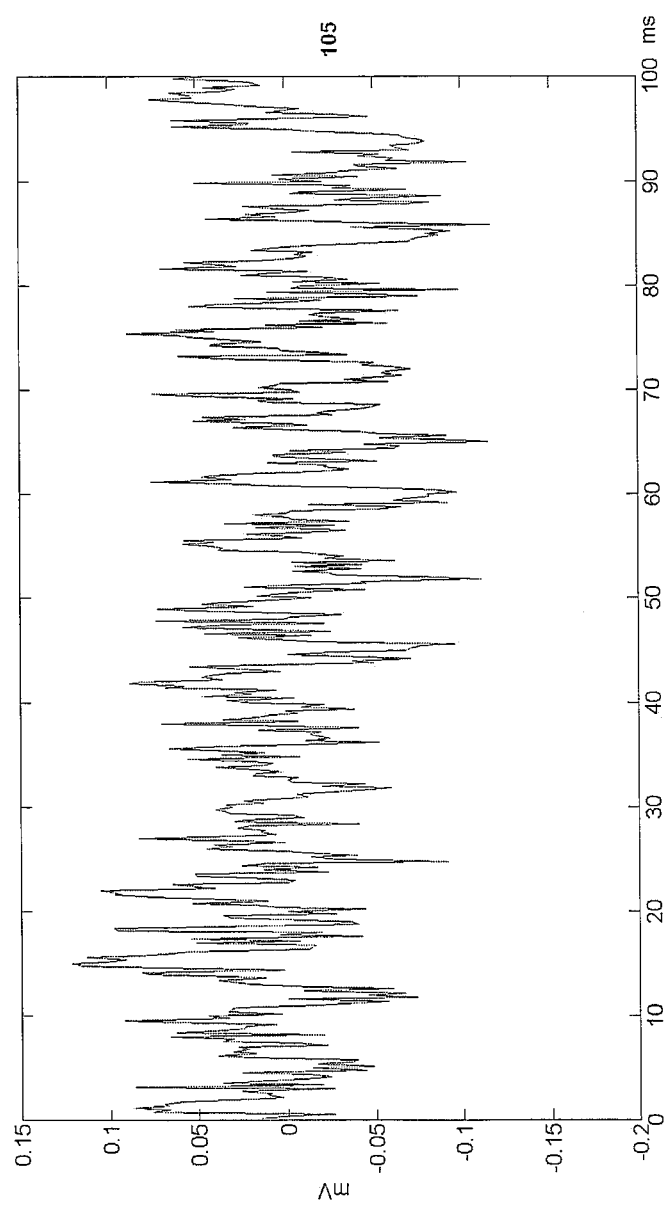
Figure 1C:
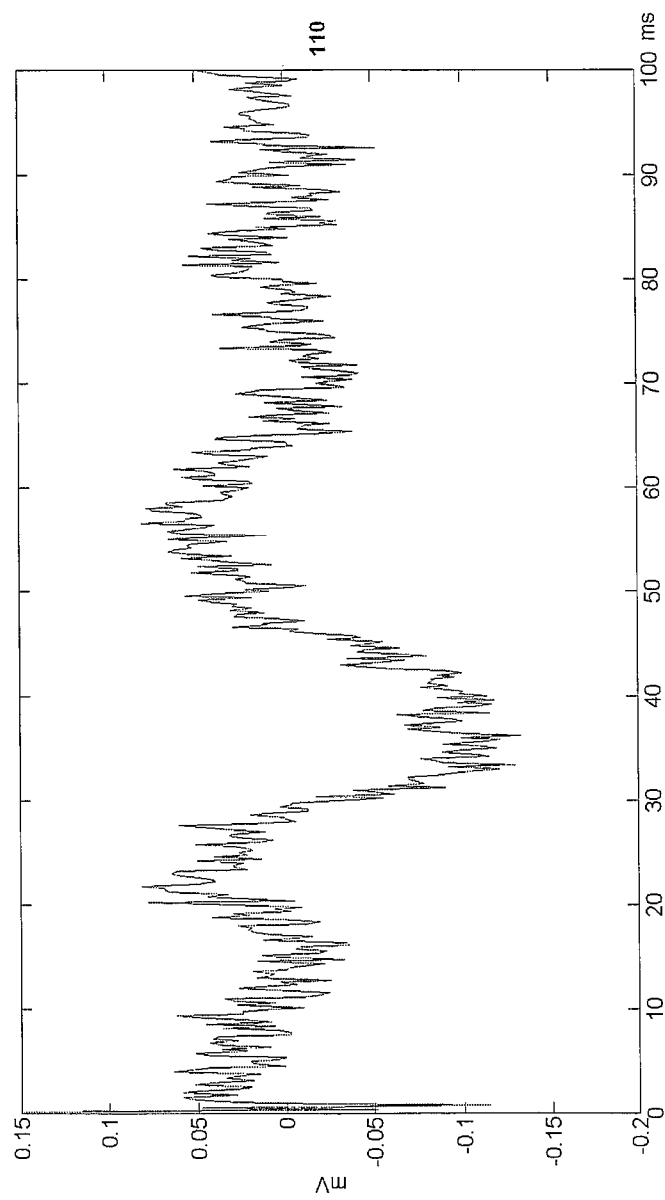

FIGS. 1A-C illustrate examples of noise signals extracted from SEP recordings. Charts 100, 105, and 110 of FIGS. 1A-C illustrate examples of measurements of voltage signals over a time interval. In these examples, voltage signal levels are shown in increments of milli-volts and time is shown in milli-seconds. As shown, charts 100, 105, and 110 show voltage signal level measurements that may fluctuate, such as about 0.05-0.20 mV, over relatively short time increments, resulting in charts that appear "choppy" as opposed to "smooth."

Figure 2A:
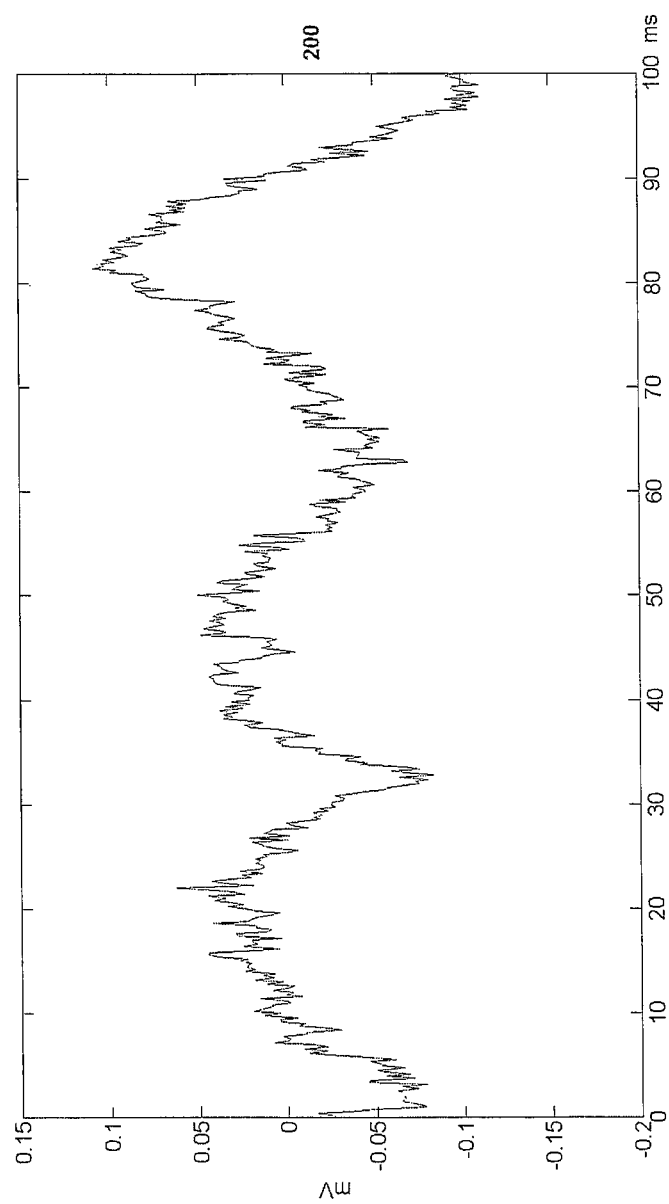
FIGS. 2A-C illustrate examples of SEP waveforms extracted from SEP recordings.
Figure 2B:
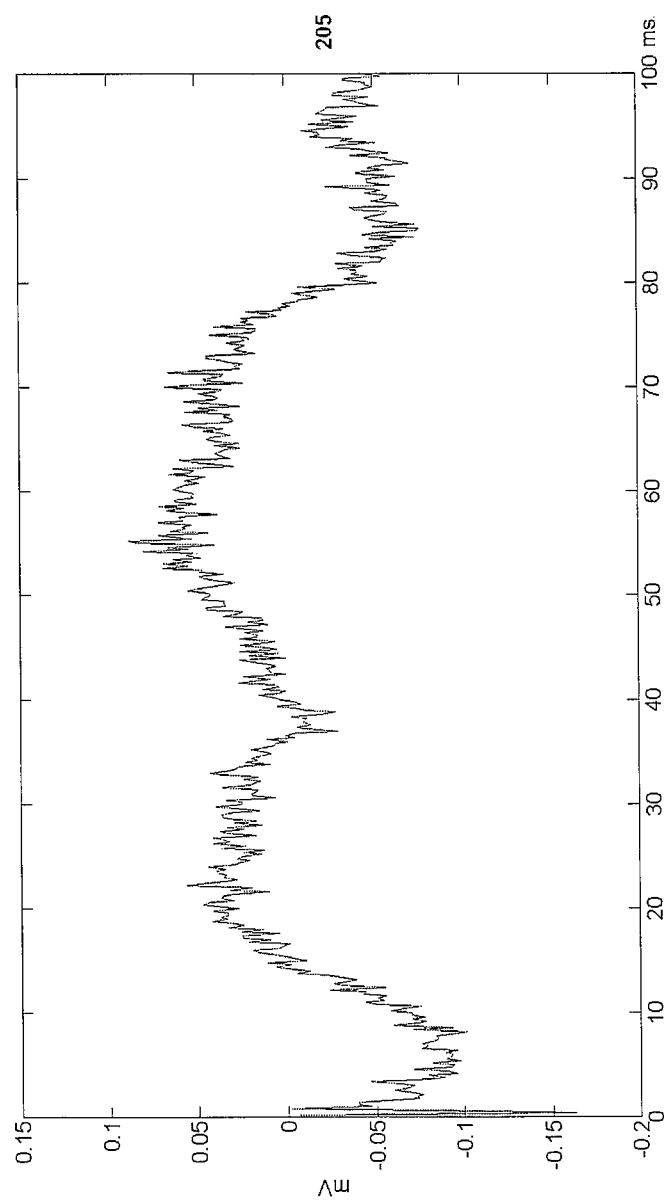
Figure 2C:
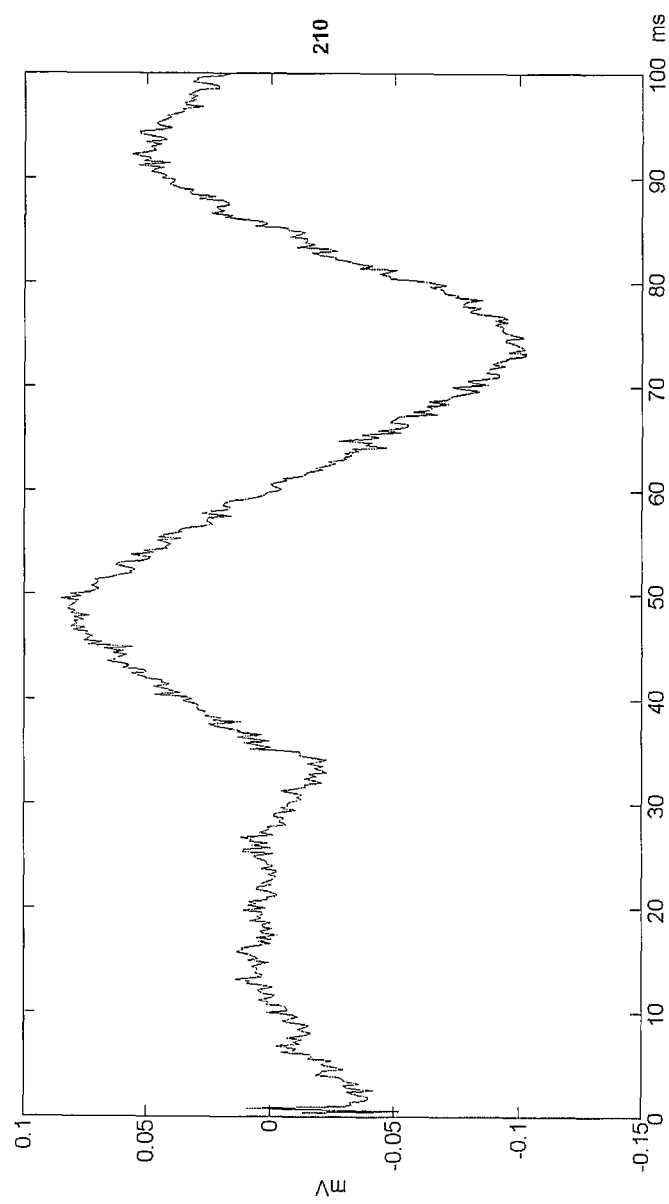

FIGS. 2A-C illustrate examples of SEP waveforms extracted from SEP recordings. Charts 200, 205, and 210 of FIGS. 2A-C illustrate examples of measurements of voltage signals over a time interval. In these examples, voltage signal level is shown in increments of milli-volts and time is shown in milli-seconds. As shown, charts 200, 205, and 210 show voltage signal level measurements that generally change amplitude less quickly over short time increments than noise signals, as shown in FIGS. 1A-C, for example. Here such time increments may be on the order of 0.1-0.2 ms. Therefore, charts 200, 205, and 210 illustrate charts that appear relatively smooth as opposed to those of choppy noise signals, as shown in charts 100, 105, and 110 of FIGS. 1A-C.

For example, at a particular time there may be artifacts, such as noise transients, with sufficient amplitude that a signal-to-noise ratio (SNR) of an SEP recording may be decreased, in some instances to a large extent. Averaging may be used to address issues such as this. For example, in some embodiments it may be possible to exclude any trace containing a signal value level greater than a specific threshold. Another technique may involve evaluating frequencies within an SEP recording. For example, a Fast Fourier Transform (FFT) of an SEP recording may be performed to determine frequencies of an SEP recording. Frequency or amplitude criteria may be applied based at least in part on FFT results for an SEP recording. For example, SEP recordings of may be rejected or omitted, as previously discussed, for example if a measured voltage signal level in a band of approximately 30- to approximately 70-Hz of an SEP recording exceeds approximately 100 uV.

Some SEP recordings may be omitted with beneficial results by an approximate 100 uV threshold; however, this is merely an example and it is not intended that claimed subject matter be limited in this respect. Nonetheless, selection of an appropriate voltage signal level threshold may be challenging. For example, an appropriate voltage signal level threshold may vary from person to person. A higher threshold may gather usable SEP recordings but signal quality may be degraded. Conversely, a lower threshold may reject noisier SEP recordings and may therefore present SEP recordings with higher quality. However, use of a lower threshold may prolong recording time, taking longer to provide neurophysiologists or clinicians with SEP composite recordings to evaluate an individual's somatosensory pathways.

A method of artifact rejection or omission based at least in part on voltage signal level thresholds may not, however, be particularly effective at detecting noise signals having low amplitude, relatively speaking, combined with SEP waveforms with low amplitude. Another method may apply amplitude discrimination whereby voltage signal levels produced are evaluated if peak voltage signal level values during a predefined time period, such as an epoch, are less than a selected voltage signal level, as discussed below with respect to FIG. 3. In such approaches, parameters based at least in part on an amplitude range in an SEP recording, or differences between two successive signal sample values may be used as thresholds for artifact rejection or omission. However, again, a challenge related to selecting appropriate threshold signal level values exists.

Approaches as previously described also may produce a small bias in SEP composite recordings obtained by averaging. For example, a noise signal at a given point in time may be independent and characterized by a symmetric, continuous distribution function with the highest probability density near zero. However, bias may occur if a distribution function has narrow peaks at relatively high-amplitude noise signal value levels and a threshold employed is relatively close to the noise amplitude signal value level. Biases may also occur if noise signals are not independently distributed at a given point in time point, for example For a technique based at least in part on applying an FFT, in one particular embodiment, SEP recordings with amplitudes that exceed a given threshold within a given range of a frequency spectrum may be rejected or omitted. However, suppose a noise signal source in an operating room environment comprises a power line which overlaps with the SEP spectrum. If so, this method may not show significant differences from a method based at least in part on amplitude signal value levels.

In one implementation, however, a method for artifact rejection or omission may utilize frequency and temporal properties of SEP waveforms and noise signal components as classification criteria to detect and reject SEP recordings. A method based at least in part on frequency and temporal properties may utilize reasonably stable parameters—median frequency or zero-cross rate, for example, as described in more detail below.

"Median frequency," as used herein, may refer to a midpoint frequency of a power spectrum for an SEP recording. "Zero-cross rate," as used herein, may refer to a rate of sign-changes (e.g., between positive and negative voltage signal value levels) along a plot of an SEP recording for a given time period. An embodiment, for example, may have a benefit in that the previously described trade-off that may occur from employing a higher amplitude versus a lower amplitude in terms of greater degradation or a longer recording period may be reduced, for example.

An embodiment of a method as discussed below may provide an SEP recording classifier for artifact rejection, for example, although claimed subject matter is not limited in scope to this particular embodiment. Nonetheless, by using frequency and temporal properties of SEP waveforms and noise components as classification criteria to reject SEP recordings, such a method may boost signal quality and reduce the number of SEP recordings for satisfactory results. Of course, claimed subject matter is not limited in scope to implementation in hardware, software or firmware. Many combinations are possible. Nonetheless, it is not intended that claimed subject matter be directed to software per se.

A method or system as described in accordance with one embodiment, for example, may be capable of detecting SEP recordings containing artifacts that may be relatively frequent or that may have relatively large amplitudes, for example. As discussed, signal averaging of SEP recordings may be utilized to extract SEP waveforms from noise signals, such as electrical signals picked up by recording electrodes, for example. Artifact rejection, however, may be used to select appropriate SEP recordings. Accordingly, such a method or system may comprise an effective tool for selecting SEP recordings with sufficient quality in an environment having noise signal sources present, such as in an operating room of a hospital or medical center.

Figure 3:
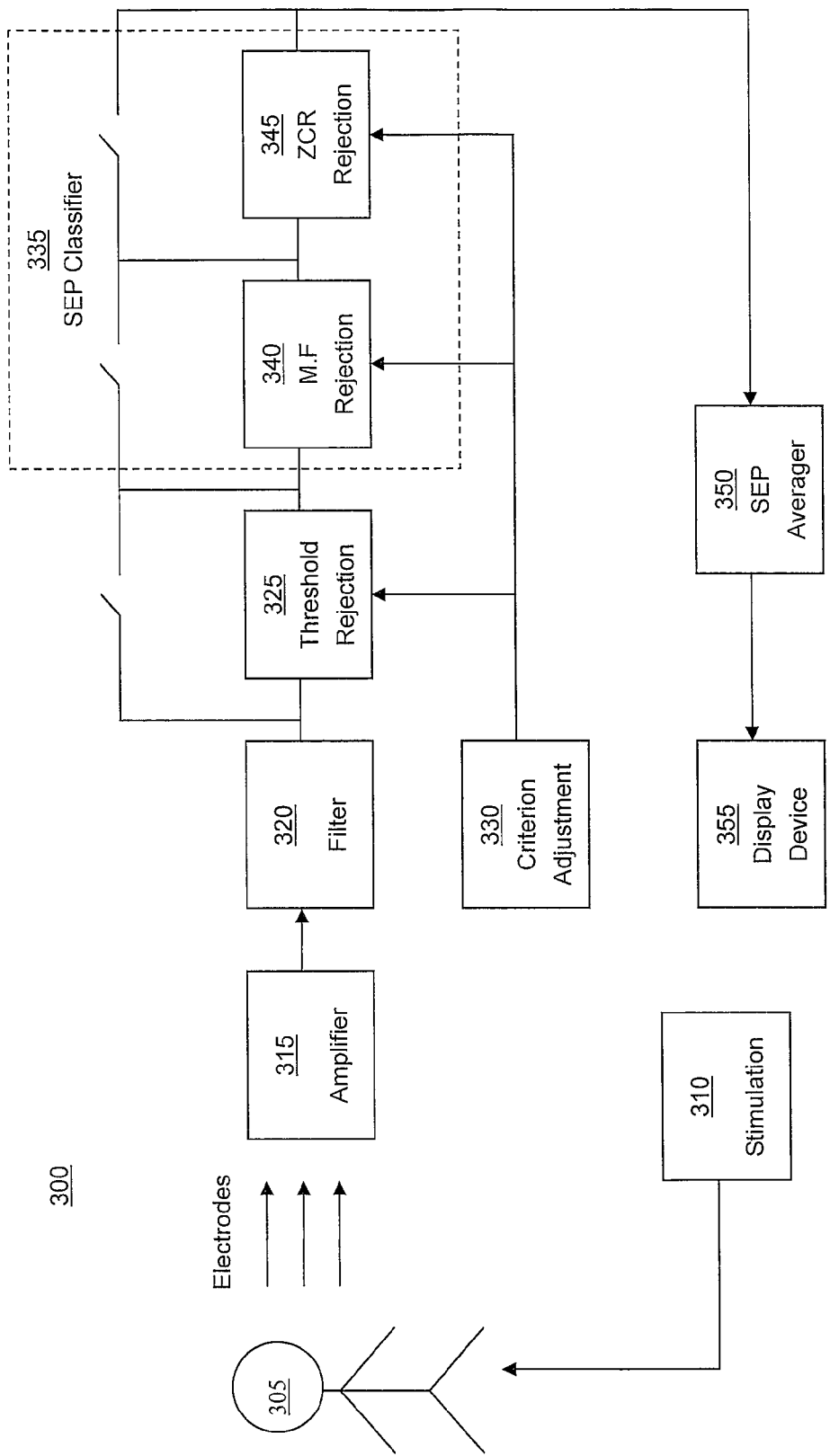
FIG. 3 is a schematic diagram of a system for artifact processing according to an implementation.

FIG. 3 is a schematic diagram of an embodiment of a system 300 for artifact rejection according to one implementation. Such a system 300 for artifact rejection may utilize several criteria, including a voltage signal level threshold criterion. For example, signals may be accepted for evaluation if peak signal value levels of an SEP recording are less than a particular signal value level. Such a method or system may provide artifact rejection in SEP detectors or monitors, for example. Such a method may be applied on unprocessed signals to reject SEP recordings based at least in part on temporal and frequency parameters, including zero-crossing rate and median frequency, in one particular embodiment, for example.

Certain SEP recordings may initially be rejected based at least in part on threshold voltages contained within such SEP recordings. Additional classification of SEP recordings may also be performed. After signal classification, SEP recordings may be rejected if determined to be undesirable. Such a method may boost signal quality for averaging into an SEP composite recording and may also use fewer SEP recordings.

Referring to FIG. 3, an individual 305 may be subjected to repetitive electrical stimuli, which may be delivered by a surface or needle electrode from an electrical stimulator 310. Such stimuli may be delivered to a periphery nerve to elicit somatosensory evoked potentials, which may be recorded in part through use of an amplifier, such as by amplifier 315. A filter 320 may be applied to also filter noise signals from an SEP recording. For example, certain frequencies which may be known to contain signals unrelated to an SEP waveform may be filtered from an SEP recording. After filtering, a filtered SEP recording may be provided to a threshold rejection element 325. Threshold rejection element 325 may, for example, reject SEP recordings having one or more peak voltage signal values greater than an upper threshold signal value. A criterion adjustment element 330 may provide such threshold signal value levels utilized by threshold rejection element 325. Criterion adjustment element 330 may, for example, dynamically adjust such threshold signal values for a given individual based at least in part on evaluation of somatosensory evoked potentials.

If an SEP recording has peak signal value levels approximately below the threshold signal value of threshold rejection element, the SEP recording may be classified by an SEP classifier 335. SEP classifier 335 may comprise a Median Frequency (M.F.) rejection element 340 and a Zero Crossing Rate (ZCR) rejection element 345, for example, in this particular embodiment.

M.F. rejection element 340 may reject an SEP recording having a median frequency that is not approximately within a selected range, as discussed below with respect to FIG. 4. A median frequency may be computed as $$\sum_{k=0}^{f_{median}} P(f_k) = \sum_{k=f_{median}}^{\frac{f_c}{2}} P(f_k)$$

where, $P(f_k)$ comprises a $k_{th}$ sample of a power spectrum of said at least one evoked potential recording, $f_c$ comprises a sampling frequency, and $f_{median}$ comprises said median frequency. In an embodiment, a threshold median frequency may be approximately within a range between 10 Hz and 150 Hz.

ZCR rejection element 345 may reject an SEP recording having a zero-crossing rate that is not approximately within a selected range, as discussed below with respect to FIGS. 5A and B.

Use of a combination of a threshold rejection element 325, an M.F. rejection element 340, and a ZCR rejection element 345, as opposed to merely a single threshold rejection element 325 may likewise provide a beneficial embodiment. A display device 355 may visually display a measured zero-crossing rate or a median frequency of an SEP recording. System 300 may therefore comprise an effective tool for selecting SEP recordings. Such a technique may be applied to unprocessed signals to select SEP recordings based at least in part on temporal and frequency parameters, including zero-crossing rate and median frequency.

Figure 4A:
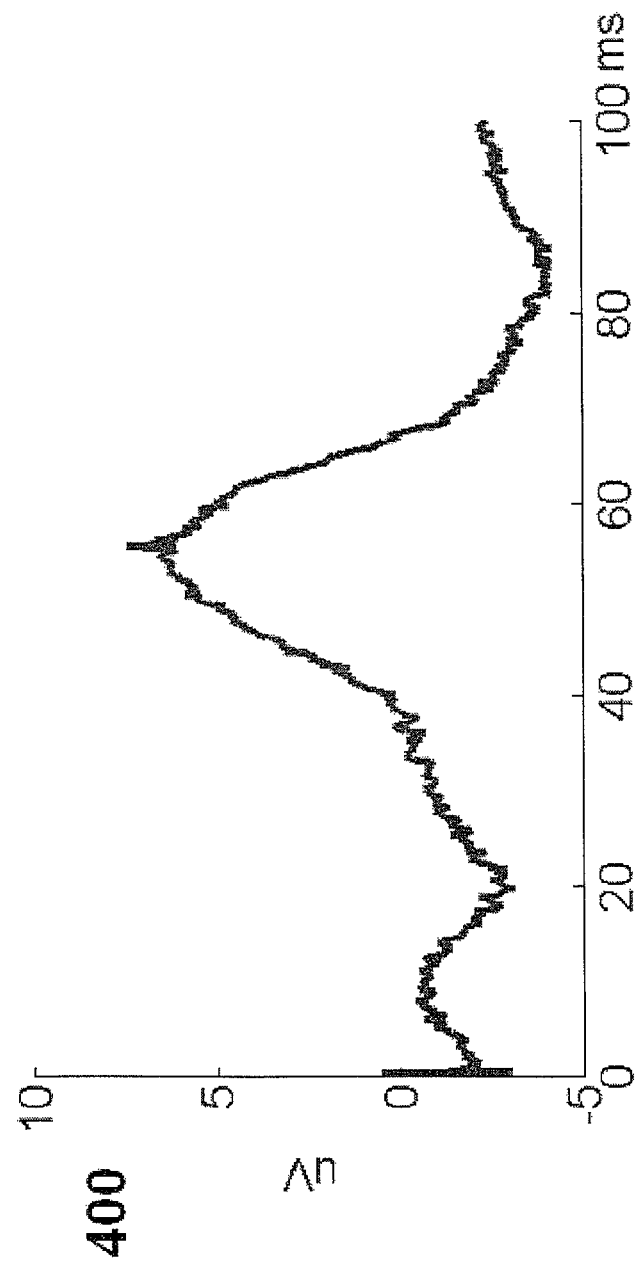
FIG. 4A illustrates an example of an SEP recording comprising noise signals according to an implementation.

FIG. 4A illustrates an example SEP recording according to one implementation. Chart 400 of FIG. 4A illustrates an SEP recording that is relatively smooth and has not been adversely affected by the presence of one or more noise signals to an extent that suggest rejection or omission.

Figure 4B:
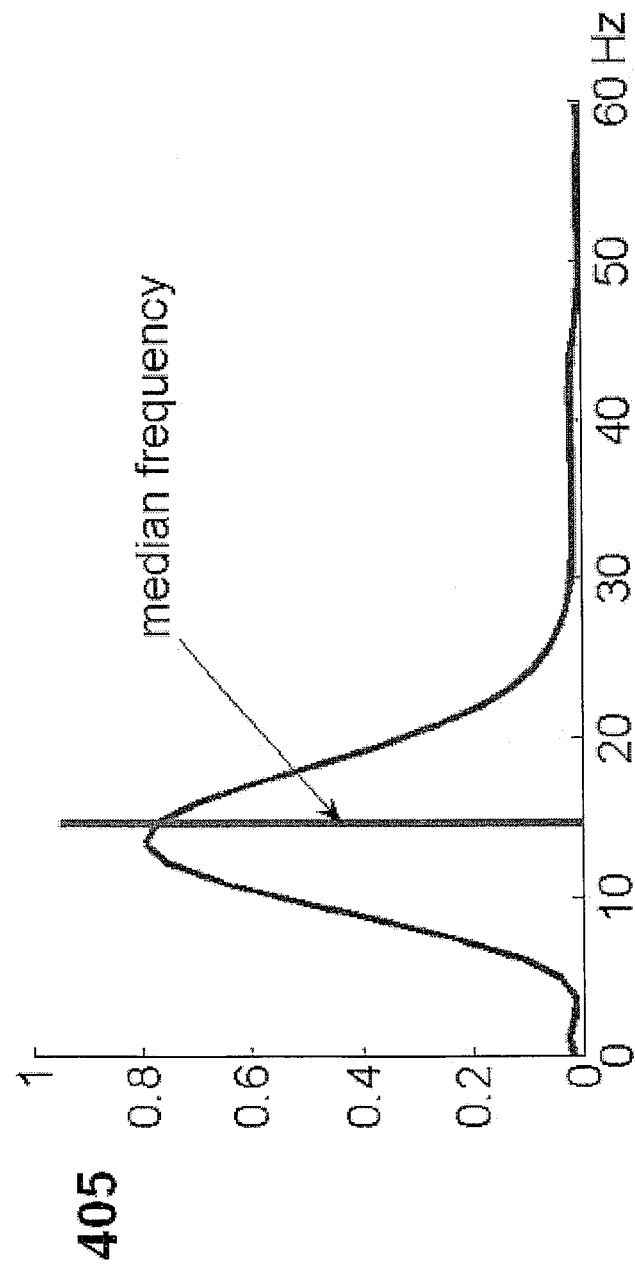
FIG. 4B illustrates a chart of a frequency spectrum for an SEP recording according to an implementation.

FIG. 4B illustrates a chart 405 of a frequency spectrum for an SEP recording according to one implementation. A frequency spectrum of an SEP recording may be calculated, in one embodiment, by, for example, performing an FFT to determine which frequencies are present in the SEP recording. A median frequency in this context comprises a midpoint of a frequency spectrum for an SEP recording and divides a power spectrum for an SEP recording into two approximately equal parts, such that half of the power spectrum is below the median frequency and half of the power spectrum is above the median frequency. Frequency characteristics of SEP waveforms may differ from frequency characteristics of noise signal waveforms. If a median frequency is equal to or below a selected criterion such as, for example, 20 Hz in the example shown in FIGS. 4A and 4B, an SEP recording may be classified as a waveform in which noise signals have not degraded an SEP waveform sufficient to result in rejection or omission. Chart 405 shows a median frequency of approximately 12 Hz for an SEP recording. In the event that a threshold median frequency comprises 20 Hz, such an SEP recording may be further processed. If, on the other hand, a median frequency shown in chart 405 for an SEP recording were greater than a threshold 20 Hz, such an SEP recording may instead be classified as a waveform in which noise signals have degraded an SEP waveform sufficient to result in rejection or omission.

Figure 4C:
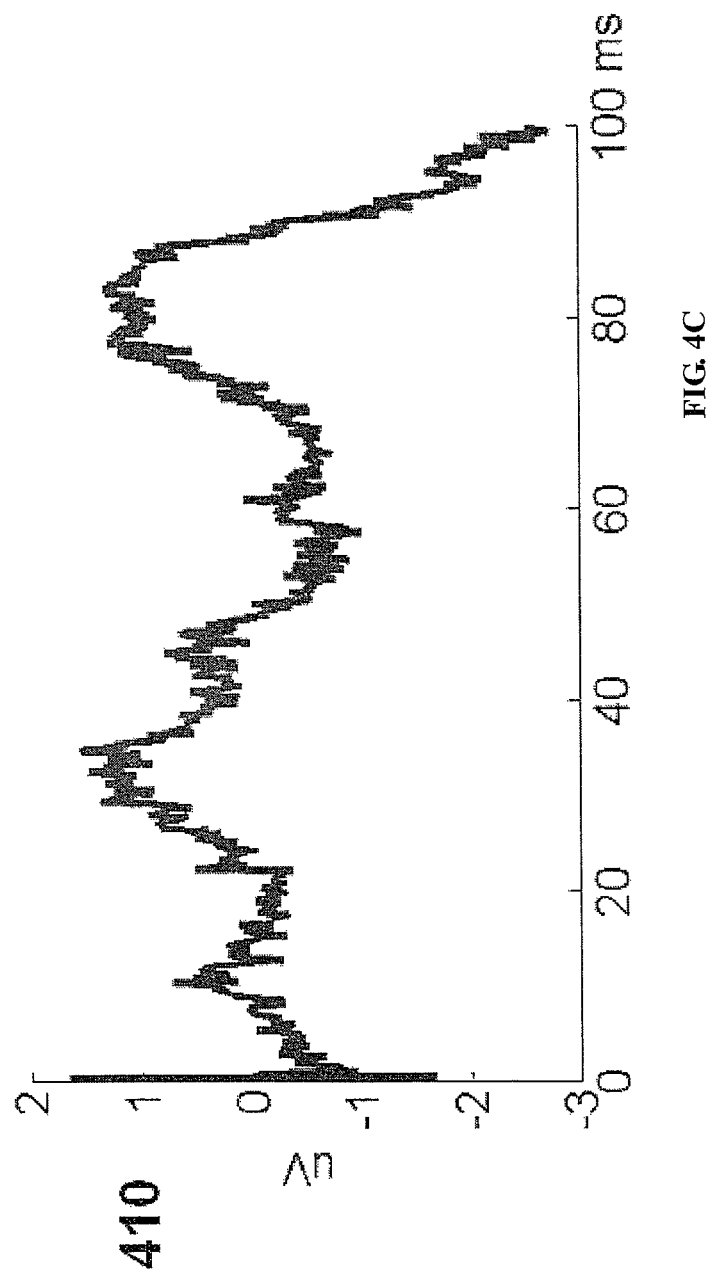
FIG. 4C illustrates another example of an SEP recording comprising noise signals according to an implementation.

FIG. 4C illustrates another example SEP recording according to one implementation. Chart 410 of FIG. 4C illustrates an SEP recording that is relatively choppy and in which noise signals have degraded an SEP waveform sufficient to result in rejection or omission.

Figure 4D:
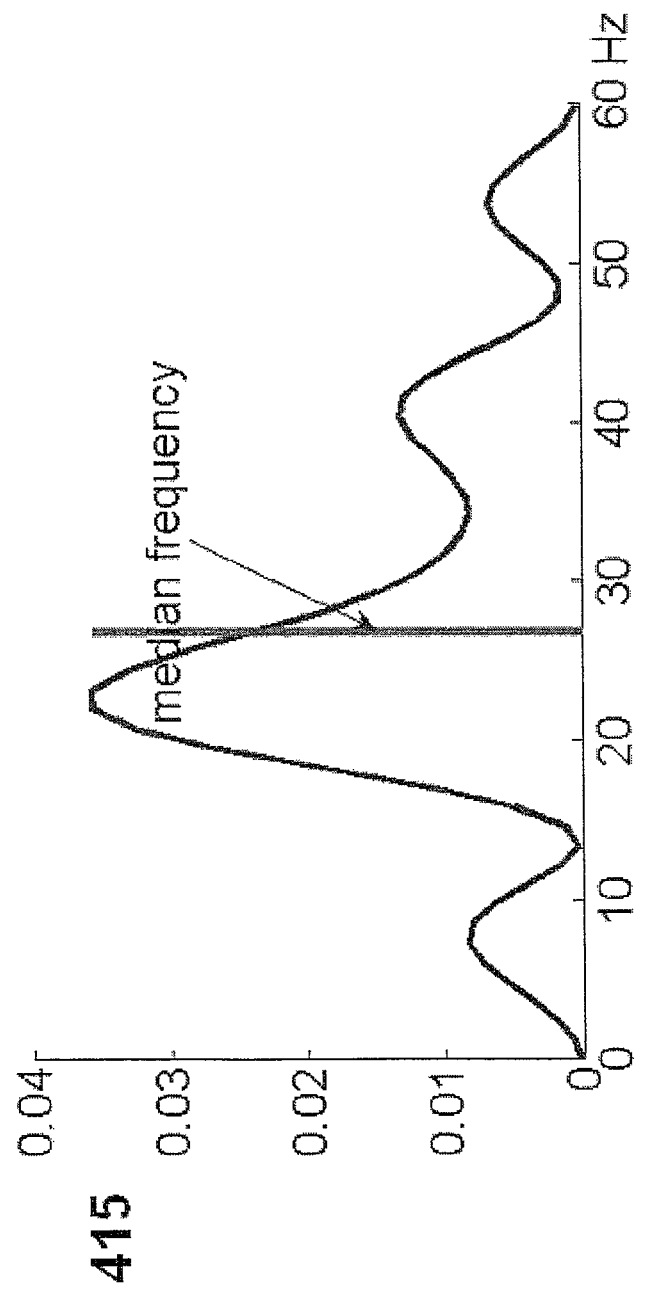
FIG. 4D illustrates another chart of a frequency spectrum for an SEP recording according to an implementation.

FIG. 4D illustrates a chart 415 of a frequency spectrum for an SEP recording according to one implementation. As illustrated, chart 415 shows that the frequency spectrum for an SEP recording shown in chart 410 has several frequency peaks. For example, chart 415 shows frequency peaks at about 8 Hz, 22 Hz, 40 Hz, and 54 Hz. Chart 415 also shows that a median frequency for an SEP recording in this example is about 22 Hz. If a threshold median frequency comprises 20 Hz, an SEP recording having this frequency spectrum may be classified as a waveform in which noise signals have degraded an SEP waveform sufficient to result in rejection or omission.

FIGS. 5A and 5B illustrate voltage signal measurements over a time period for an SEP recording according to one implementation. Charts 500 and 505 of FIGS. 5A and 5B, respectively, illustrate that voltage signal value levels of SEP recordings may fluctuate between a positive voltage value (measured in uV in this example) and a negative voltage value during a given time period. In this example, an observed time period is 100 milli-seconds. Of course, claimed subject matter is not limited in scope in these respects. This is merely an example provided for purposes of illustration.

FIGS. 5A and 5B show for a particular embodiment a calculation of zero-crossing points in SEP recordings. A zero-crossing rate in this context refers to the rate of sign-changes along an SEP recording. For a particular embodiment, for example, it may be computed or calculated as $$zcr = \frac{1}{T}\sum_{t=0}^{T-1} \Pi\{s_t s_{t-1} < 0\}$$

where s is the SEP recording of length T and an indicator function $\Pi\{A\}$ is "1" if its argument A is true and "0" if otherwise; however, again, claimed subject matter is not limited in scope in this respect. Other approaches to calculating zero crossings are possible and are intended to be included within the scope of claimed subject matter.

A zero-crossing rate may be used as a primitive pitch detection approach in one embodiment, for example. If, for example, a zero-crossing rate is less than a threshold value, an SEP recording may be classified as a waveform in which noise signals have not degraded an SEP waveform sufficient to result in rejection or omission. In one example, a threshold zero-crossing rate value may be approximately within a range of 1-100 zero-crossings for a given time period.

A zero-crossing rate criterion may be utilized to classify an SEP recording regarding level of noise signals affecting the recording. Chart 500 of FIG. 5A illustrates an SEP recording having only six zero-crossings during a 100 milli-second time period. If, for example, a ZCR threshold value comprises 15 zero-crossings, an SEP recording depicted in chart 500 may be classified as not significantly influenced or degraded by noise signals.

Chart 505 of FIG. 5B, on the other hand, illustrates an SEP recording having more than 40 zero-crossings during a 100 milli-second time period. If, for example, a zero-crossing rate threshold value comprises 15 zero-crossings, an SEP recording depicted in chart 505 may be classified as being influenced by noise signals and may, in some embodiments, for example, be removed from further processing.

Median frequency and zero-crossing rate be computed for an SEP recording. If such values exceed selected thresholds, such an SEP recording may be omitted. If, on the other hand, such values do not exceed selected thresholds, the SEP recording may be processed further. A large sample may be utilized to determine threshold values of median frequency and zero-crossing rate in one particular embodiment. Alternatively, such threshold values may be set or selected by users in an alternate embodiment.

A frequency property may be considered as a reasonably stable indicator of an SEP recording. A spectral range of an SEP waveform may be stably different from that of noise signals, for example. Likewise, median frequency may be an indicator of a suitable SEP waveform. Although median frequency may comprise a reliable characteristic, zero-crossing rate may also be used as a temporal indicator in combination with median frequency to achieve further refinement in some embodiments.

Application of an SEP classifier for artifact rejection based at least in part on median frequency and zero-crossing rate may in some situations increase reliability of SEP recordings and spinal cord monitoring. By using both frequency and a temporal property of SEP waveforms and noise components as classification criteria to reject SEP recordings, such an embodiment may boost signal quality and employ fewer SEP recordings for a composite.

Figure 6:
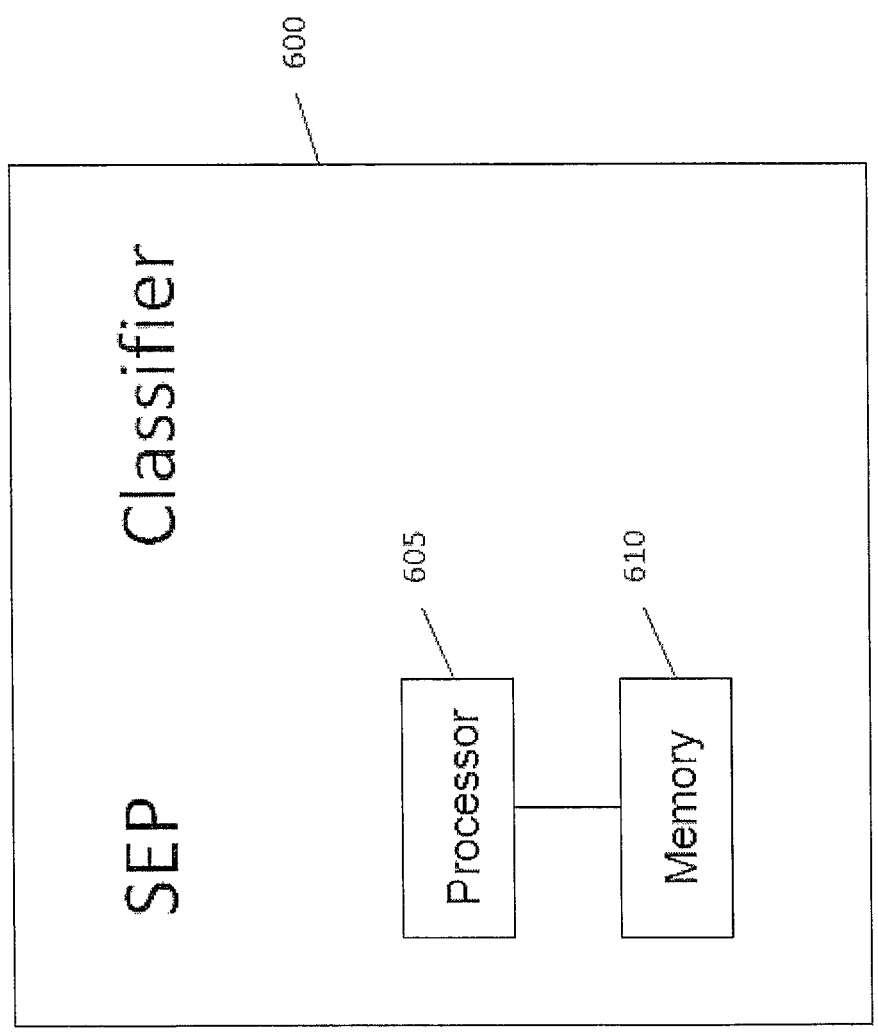
FIG. 6 illustrates an SEP classifier according to an implementation.

FIG. 6 illustrates an SEP classifier 600 according to one implementation. As shown, SEP classifier 600 may include a processor 605 and a memory 610. Memory 610 may store instructions executable by processor 605 so that processor 605 is able to classify SEP recordings based at least in part on median frequency or zero-crossing rate, for example.

Methodologies described herein may be implemented by various approaches depending at least in part upon applications according to particular features or examples. For example, such methodologies may be implemented in hardware, firmware, software, or any combinations thereof. However, it is not intended that claimed subject matter cover software per se. In a hardware implementation, for example, a processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, or other devices units designed to perform functions such as those described herein or any combinations thereof.

Likewise, in some embodiments, methodologies may be implemented with modules (e.g., procedures, functions, and so on) that perform functions described herein or any combination thereof. Any machine readable medium tangibly embodying instructions may be used in implementing such methodologies, for example. In an embodiment, for example, software or code may be stored in a memory and executed by a processing unit. Memory may be implemented within a processing unit and/or external to the processing unit. As used herein the term "memory" refers to any type of long term, short term, volatile, nonvolatile, or other memory and is not to be limited to any particular type of memory or number of memories, or type of media upon which memory is stored.

Likewise, a storage medium may take the form of an article of manufacture. A storage media may comprise any available media that may be accessed by a computer, computing platform, computing device, or the like. By way of example but not limitation, a computer-readable medium may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer, computing platform or computing device.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice-versa. The foregoing is not intended to be an exhaustive list of all examples in which a change in state for a binary one to a binary zero or vice-versa in a memory device may comprise a transformation, such as a physical transformation. Rather, the foregoing are intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

While there has been illustrated or described what are presently considered to be example features, it will be understood by those skilled in the art that various other modifications may be made, or equivalents may be substituted, without departing from claimed subject matter. Additionally, many modifications may be made to adapt a particular situation to teachings of claimed subject matter without departing from concepts described herein. Therefore, it is intended that claimed subject matter not be limited to particular examples disclosed, but that such claimed subject matter may also include all aspects falling within the scope of appended claims, or equivalents thereof.

What is claimed is:

1. A method, comprising:
   using a computing platform,
   classifying at least one evoked potential recording based at least in part on a median frequency of said at least one evoked potential recording and a measured zero-crossing rate of said at least one evoked potential recording; and
   rejecting said at least one evoked potential recording based at least in part on said median frequency and said zero-crossing rate being approximately within a particular range, wherein a threshold median frequency is approximately within a range between 10 Hz and 150 Hz.

2. The method of claim 1, further comprising recording said at least one evoked potential recording in response to one or more somatosensory stimulus.

3. The method of claim 1, wherein said at least one evoked potential recording is obtained from a human or animal body.

4. The method of claim 1, further comprising averaging at least two acceptable evoked potential recordings to generate a composite evoked potential recording.

5. The method of claim 1, wherein said median frequency is computed as $$\sum_{k=0}^{f_{median}} P(f_k) = \sum_{k=f_{median}}^{\frac{f_c}{2}} P(f_k)$$

where, $P(f_k)$ comprises a $k_{th}$ sample of a power spectrum of said at least one evoked potential recording, $f_c$ comprises a sampling frequency, and $f_{median}$ comprises said median frequency.

6. The method of claim 1, further comprising presenting said median frequency on a display device.

7. The method of claim 1, wherein said zero-crossing rate is computed as $$zcr = \frac{1}{T}\sum_{t=0}^{T-1} \Pi\{s_t s_{t-1} < 0\}$$

where s comprises said at least one evoked potential recording of time length T and an indicator function $\Pi\{A\}$ is 1 if argument A is true and 0 if otherwise.

8. The method of claim 7, wherein a threshold zero-crossing rate is approximately within a range of 1 to 100 during said time length T.

9. The method of claim 8, wherein said threshold zero-crossing rate is user-selectable.

10. The method of claim 8, wherein at least one evoked potential recording is classified as rejected if the measured zero-crossing rate is substantially equal to or higher than said threshold zero-crossing rate.

11. The method of claim 1, further comprising presenting said measured zero-crossing rate on a display device.

12. The method of claim 1, wherein said evoked potential recording comprises a somatosensory evoked potential (SEP) recording.

13. The method of claim 1, wherein said evoked potential recording comprises at least one of the following: an electroencephalogram, nerve conduction recording, visual evoked potentials, audio evoked potentials, or any combination thereof.

14. The method of claim 1, further comprising receiving one or more binary digital signals representative of said at least one evoked potential recording.

15. A method, comprising:
using a computing platform,
classifying at least one evoked potential recording based at least in part on a median frequency of said at least one evoked potential recording and a measured zero-crossing rate of said at least one evoked potential recording; and
rejecting said at least one evoked potential recording based at least in part on said median frequency and said zero-crossing rate being approximately within a particular range;
wherein said median frequency is computed as $$\sum_{k=0}^{f_{median}} P(f_k) = \sum_{k=f_{median}}^{\frac{f_c}{2}} P(f_k)$$

where, $P(f_k)$ comprises a $k_{th}$ sample of a power spectrum of said at least one evoked potential recording, $f_c$ comprises a sampling frequency, and $f_{median}$ comprises said median frequency, a threshold median frequency being approximately within a range between 10 Hz and 150 Hz.

16. The method of claim 15, wherein said threshold median frequency is user-selectable.

17. The method of claim 15, wherein said at least one evoked potential recording is classified as rejected if said median frequency is substantially equal to or higher than said threshold median frequency.

18. An apparatus, comprising:
a computing platform capable of:
classifying at least one evoked potential recording based at least in part on a median frequency of said at least one evoked potential recording and a measured zero-crossing rate of said at least one evoked potential recording; and
rejecting said at least one evoked potential recording based at least in part on said median frequency and said zero-crossing rate being approximately within a particular range, wherein a threshold median frequency is approximately within a range between 10 Hz and 150 Hz.

19. The apparatus of claim 18, wherein said computing platform is capable of averaging at least two acceptable evoked potential recordings to generate a composite evoked potential recording.

20. The apparatus of claim 18, wherein said evoked potential recording comprises a somatosensory evoked potential (SEP) recording.

21. The apparatus of claim 18, wherein said computing platform is capable of computing said median frequency as $$\sum_{k=0}^{f_{median}} P(f_k) = \sum_{k=f_{median}}^{\frac{f_c}{2}} P(f_k)$$

where, $P(f_k)$ comprises a $k_{th}$ sample of a power spectrum of said at least one evoked potential recording, $f_c$ comprises a sampling frequency, and $f_{median}$ comprises said median frequency.

22. The apparatus of claim 18, wherein said computing platform is capable of computing said zero-crossing rate as $$zcr = \frac{1}{T}\sum_{t=0}^{T-1} \Pi\{s_t s_{t-1} < 0\}$$

where s comprises said at least one evoked potential recording of length T and an indicator function $\Pi\{A\}$ is 1 if argument A is true and 0 if otherwise.

23. An article comprising: a storage medium having stored thereon instructions executable by a processor to:
classify at least one evoked potential recording based at least in part on a median frequency of said at least one evoked potential recording and a measured zero-crossing rate of said at least one evoked potential recording; and
reject said at least one evoked potential recording based at least in part on said median frequency and said zero-crossing rate being approximately within a particular range, wherein a threshold median frequency is approximately within a range between 10 Hz and 150 Hz.

24. The article of claim 23, wherein said instructions are further executable by said processor to average at least two acceptable evoked potential recordings to generate a composite evoked potential recording.

25. The article of claim 23, wherein said instructions are further executable by said processor to record said at least one evoked potential recording in response to one or more somatosensory stimulus.

26. The article of claim 23, wherein said instructions are further executable by said processor to compute said median frequency as $$\sum_{k=0}^{f_{median}} P(f_k) = \sum_{k=f_{median}}^{\frac{f_c}{2}} P(f_k)$$

where, $P(f_k)$ comprises a $k_{th}$ sample of a power spectrum of said at least one evoked potential recording, $f_c$ comprises a sampling frequency, and $f_{median}$ comprises said median frequency.

27. The article of claim 23, wherein said instructions are further executable by said processor to compute said zero-crossing rate as $$zcr = \frac{1}{T}\sum_{t=0}^{T-1} \Pi\{s_t s_{t-1} < 0\}$$

where s comprises said at least one evoked potential recording of length T and an indicator function $\Pi\{A\}$ is 1 if argument A is true and 0 if otherwise.

* * * * *